(12) United States Patent
Babu

(10) Patent No.: US 11,952,333 B2
(45) Date of Patent: Apr. 9, 2024

(54) INTEGRATED SYSTEMS AND METHODS FOR PRODUCING 1,3-BUTADIENE VIA EXTRACTIVE DISTILLATION, DISTILLATION, AND/OR SELECTIVE HYDROGENATION

(71) Applicant: SABIC GLOBAL TECHNOLOGIES B.V., Bergen op Zoom (NL)

(72) Inventor: Mamilla Sekhar Babu, Sittard (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 17/636,535

(22) PCT Filed: Aug. 10, 2020

(86) PCT No.: PCT/IB2020/057526
§ 371 (c)(1),
(2) Date: Feb. 18, 2022

(87) PCT Pub. No.: WO2021/048655
PCT Pub. Date: Mar. 18, 2021

(65) Prior Publication Data
US 2022/0267234 A1 Aug. 25, 2022

Related U.S. Application Data

(60) Provisional application No. 62/900,409, filed on Sep. 13, 2019.

(51) Int. Cl.
*C07C 5/09* (2006.01)
(52) U.S. Cl.
CPC .................. *C07C 5/09* (2013.01)
(58) Field of Classification Search
CPC .... C07C 5/09; C07C 5/22; C07C 7/04; C07C 7/08; C07C 11/167; C07C 7/005;
(Continued)

(56) References Cited

U.S. PATENT DOCUMENTS

| | | | |
|---|---|---|---|
| 2,993,841 | A | 7/1961 | Sarno |
| 3,000,794 | A | 9/1961 | Tschopp |

(Continued)

FOREIGN PATENT DOCUMENTS

| | | |
|---|---|---|
| CN | 1671638 | 9/2005 |
| CN | 101195560 | 6/2008 |

(Continued)

OTHER PUBLICATIONS

"Butadiene Extraction Process : Field of the Disclosure" Provisional Patent Application, Client Reference No. 2009PTR004.

(Continued)

*Primary Examiner* — Sharon Pregler
(74) *Attorney, Agent, or Firm* — Norton Rose Fulbright US LLP

(57) ABSTRACT

Systems and methods for producing 1,3-butadiene from a $C_4$ hydrocarbon mixture are disclosed. The $C_4$ hydrocarbon mixture comprising 1,3-butadiene, $C_4$ acetylenes, and other $C_4$ hydrocarbons is processed in an extractive distillation column to produce a crude 1,3-butadiene stream that comprises 1,3-butadiene, and $C_4$ acetylenes including vinyl acetylene and ethyl acetylene. The crude 1,3-butadiene stream is subsequently distilled in the first distillation column, and the bottom stream of the first distillation column is further distilled in a second distillation column to produce an overhead stream comprising primarily 1,3-butadiene. A side stream comprising primarily $C_4$ acetylenes is withdrawn from the second distillation column and processed in a selective hydrogenation unit to produce additional 1,3-butadiene.

20 Claims, 2 Drawing Sheets

(58) Field of Classification Search
CPC . C07C 7/167; C07C 2521/04; C07C 2523/44; B01D 3/40
See application file for complete search history.

(56) References Cited

U.S. PATENT DOCUMENTS

| | | | |
|---|---|---|---|
| 3,349,010 A | 10/1967 | Plaster | |
| 3,436,438 A | 4/1969 | Takao et al. | |
| 3,617,493 A | 11/1971 | Wirth et al. | |
| 3,772,158 A | 11/1973 | Sarno | |
| 4,038,156 A | 7/1977 | Knott et al. | |
| 4,049,742 A | 9/1977 | Weitz et al. | |
| 4,292,141 A | 9/1981 | Lindner et al. | |
| 4,556,461 A | 12/1985 | Ogura et al. | |
| 4,831,200 A * | 5/1989 | Debras | C10G 65/04 526/912 |
| 4,859,286 A | 8/1989 | Kaibel et al. | |
| 7,829,752 B2 | 11/2010 | Baumgartner et al. | |
| 7,993,435 B2 | 8/2011 | Stell et al. | |
| 8,083,932 B2 | 12/2011 | Baumgartner et al. | |
| 8,252,150 B1 * | 8/2012 | Hsu | B01D 3/40 585/326 |
| 9,062,262 B2 | 6/2015 | Lee et al. | |
| 9,505,679 B2 | 11/2016 | Fritz et al. | |
| 9,630,891 B2 | 4/2017 | Schmidt et al. | |
| 9,650,576 B2 | 5/2017 | Akhras et al. | |
| 9,670,418 B2 | 6/2017 | Schmidt et al. | |
| 9,725,657 B2 | 8/2017 | Sirota | |
| 2006/0021911 A1 | 2/2006 | Adrian et al. | |
| 2006/0249428 A1 | 11/2006 | Stell et al. | |
| 2009/0050530 A1 | 2/2009 | Spicer et al. | |
| 2014/0100399 A1 * | 4/2014 | Brummer | C07C 5/09 585/259 |
| 2019/0071375 A1 | 3/2019 | Yachi | |

FOREIGN PATENT DOCUMENTS

| | | |
|---|---|---|
| CN | 101239880 | 8/2008 |
| CN | 102381920 | 3/2012 |
| CN | 102781892 | 11/2012 |
| CN | 102886262 | 1/2013 |
| CN | 104812726 | 7/2015 |
| CN | 103958647 | 7/2017 |
| CN | 108137442 | 6/2018 |
| CN | 108779044 | 11/2018 |
| EP | 3438079 | 2/2019 |
| JP | S6327441 | 2/1988 |
| KR | 100760720 | 10/2007 |
| WO | WO 2001/085656 | 11/2001 |

OTHER PUBLICATIONS

International Search Report and Written Opinion issued in Corresponding PCT Application No. PCT/IB2020/057526, dated Nov. 16, 2020.

Lei et al., "Extractive Distillation: A Review" Separation and Purification Reviews 2003, 32(2):121-213.

Office Action issued in corresponding Chinese Application No. 2020800714128, dated Apr. 19, 2023.

* cited by examiner

INTEGRATED SYSTEMS AND METHODS FOR PRODUCING 1,3-BUTADIENE VIA EXTRACTIVE DISTILLATION, DISTILLATION, AND/OR SELECTIVE HYDROGENATION

CROSS REFERENCE TO RELATED APPLICATIONS

This application is a national phase application under 35 U.S.C. § 371 of International Application No. PCT/IB2020/057526, filed Aug. 10, 2020, which claims the benefit of priority of U.S. Provisional Patent Application No. 62/900,409 filed Sep. 13, 2019, the contents of which applications are hereby incorporated by reference in their entirety.

FIELD OF INVENTION

The present invention generally relates to systems and methods for producing 1,3-butadiene. More specifically, the present invention relates to systems and methods for producing 1,3-butadiene from $C_4$ hydrocarbons using an integrated process of extractive distillation, distillation, and/or hydrogenation.

BACKGROUND OF THE INVENTION 1,3-butadiene is a valuable chemical that can be used as a raw material in many chemical production processes. For instance, 1,3-butadiene can be used to produce polybutadiene, which is the main component of synthetic rubber. Furthermore, butadiene can be used for making adiponitrile, a nylon intermediate, via a hydrocyanation process.

1,3-butadiene is produced via various processes including extraction from $C_4$ raffinate of steam crackers, dehydrogenation of n-butane, and dehydrogenation of butenes. In the process of extractive distillation of $C_4$ raffinate from steam crackers, two-step extractive distillation, each step with different solvent-to-feed ratio and operating conditions, is used due to close boiling points of $C_4$ hydrocarbons in the $C_4$ raffinate. In the two-step extractive distillation process, the effluent stream from the first extractive distillation column comprising butadiene and $C_4$ acetylenes is flowed to the second extractive distillation column for separation of $C_4$ acetylenes from the butadiene.

However, extractive distillation is generally a high cost process. The use of two extractive distillation columns not only requires high capital expenditure but also high operating costs for materials and energy for producing 1,3-butadiene. Furthermore, the two-step extractive distillation method does not fully use the $C_4$ acetylenes for producing 1,3-butadiene, resulting in low production efficiency for the process.

Overall, while the methods of producing 1,3-butadiene from a $C_4$ hydrocarbon mixture exist, the need for improvements in this field persists in light of at least the aforementioned drawbacks for the conventional methods.

BRIEF SUMMARY OF THE INVENTION

A solution to at least some of the above-mentioned problems associated with the methods of producing 1,3-butadiene from a $C_4$ hydrocarbon mixture has been discovered. The solution resides in a method of producing 1,3-butadiene that comprises one extractive distillation step followed by a distillation step and a selective hydrogenation step. This method uses an extractive distillation step coupled with a distillation step to separate 1,3-butadiene from other $C_4$ hydrocarbons, thereby reducing capital expenditure, materials, and energy costs for producing 1,3-butadiene compared to conventional methods that include two extractive distillation steps. Additionally, this method uses $C_4$ acetylenes separated from the $C_4$ hydrocarbons to produce additional 1,3-butadiene via selective hydrogenation, resulting in higher production efficiency for 1,3-butadiene. Therefore, the method of the present invention provides a technical solution to at least some of the problems associated with the conventional methods of producing 1,3-butadiene.

Embodiments of the invention include a method of producing 1,3-butadiene. The method comprises extractive distillation of a $C_4$ hydrocarbon feed to form a crude butadiene stream comprising 1,3-butadiene and $C_4$ acetylenes. The method comprises distilling, by one or more distillation columns, the crude butadiene stream. The method comprises withdrawing, from the one or more distillation columns, a side stream comprising primarily the $C_4$ acetylenes. The method further comprises hydrogenating at least some of the $C_4$ acetylenes of the side stream to produce 1,3-butadiene in a product stream.

Embodiments of the invention include a method of producing 1,3-butadiene. The method comprises extractive distilling of a $C_4$ hydrocarbon feed that comprises one or more butanes, isobutane, 1-butene, 2-butenes, methyl acetylene, 1,2-butadiene, 1,3-butadiene, vinyl acetylene, ethyl acetylene, $C_5+$ hydrocarbons, or combinations thereof to form a crude butadiene stream comprising 1,3-butadiene, vinyl acetylene, ethyl acetylene, $C_5+$ hydrocarbons, or combinations thereof. The method comprises distilling, by one or more distillation columns, the crude butadiene stream. The method further comprises withdrawing, from the one or more distillation columns, a side stream comprising primarily the vinyl acetylene, and/or the ethyl acetylene. The method further still comprises selectively hydrogenating at least some of the vinyl acetylene, and/or the ethyl acetylene of the side stream to produce 1,3-butadiene in a product stream.

Embodiments of the invention include a method of producing 1,3-butadiene. The method comprises extractive distilling of $C_4$ hydrocarbon feed that comprises one or more butanes, 1,2 butadiene, 1,3 butadiene, vinyl acetylene, and ethyl acetylene to form a crude butadiene stream comprising 1,3 butadiene, vinyl acetylene, and ethyl acetylene. The method comprises distilling, in a first distillation column, the crude butadiene stream to form a first overhead stream comprising primarily methyl acetylene and a first bottom stream comprising 1,3-butadiene, vinyl acetylene, ethyl acetylene, $C_5+$ hydrocarbons, or combinations thereof. The method further comprises distilling, in a second distillation column, the first bottom stream to produce a second overhead stream comprising primarily 1,3 butadiene and second bottom stream comprising primarily $C_5+$ hydrocarbons. The method further comprises withdrawing, from the second distillation column, a side stream comprising primarily vinyl acetylene, and/or ethyl acetylene. The method further still comprises selectively hydrogenating at least some of the vinyl acetylene, and/or the ethyl acetylene of the side stream to produce a 1,3 butadiene in a product stream.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, include any measurable decrease or complete inhibition to achieve a desired result.

The term "effective," as that term is used in the specification and/or claims, means adequate to accomplish a desired, expected, or intended result.

The term "$C_n+$ hydrocarbon," wherein n is a positive integer, e.g. 1, 2, 3, 4, or 5, as that term is used in the specification and/or claims, means any hydrocarbon having at least n number of carbon atom(s) per molecule.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

Currently, a conventional method of producing 1,3-butadiene from a $C_4$ hydrocarbon mixture produced by a steam cracker includes two extractive distillation steps, in which the first extractive distillation step includes separating the $C_4$ hydrocarbon stream into (1) an effluent comprising butadiene and $C_4$ acetylenes and (2) a stream comprising other $C_4$ hydrocarbons and the second extractive distillation step includes separating the effluent stream into a 1,3-butadiene stream and a $C_4$ acetylene stream. The conventional two step extractive distillation steps require high capital expenditure, materials, and energy costs. Additionally, the $C_4$ acetylene is not fully utilized for producing 1,3-butadiene, resulting in low production efficiency. The present invention provides a solution to at least some of these problems. The solution is premised on a method of producing 1,3-butadiene that comprises one extractive distillation step followed by a distillation step and a selective hydrogenation step. By eliminating one of the extractive distillation steps, the discovered method is capable of reducing the capital expenditure, materials, and energy costs for producing 1,3-butadiene compared to the conventional methods. Furthermore, the discovered method produces additional 1,3-butadiene via selectively hydrogenating $C_4$ acetylene separated from the distillation step, resulting in increased production efficiency for 1,3-butadiene compared to the conventional methods. These and other non-limiting aspects of the present invention are discussed in further detail in the following sections.

A. System for Producing 1,3-Butadiene

Figure 1:
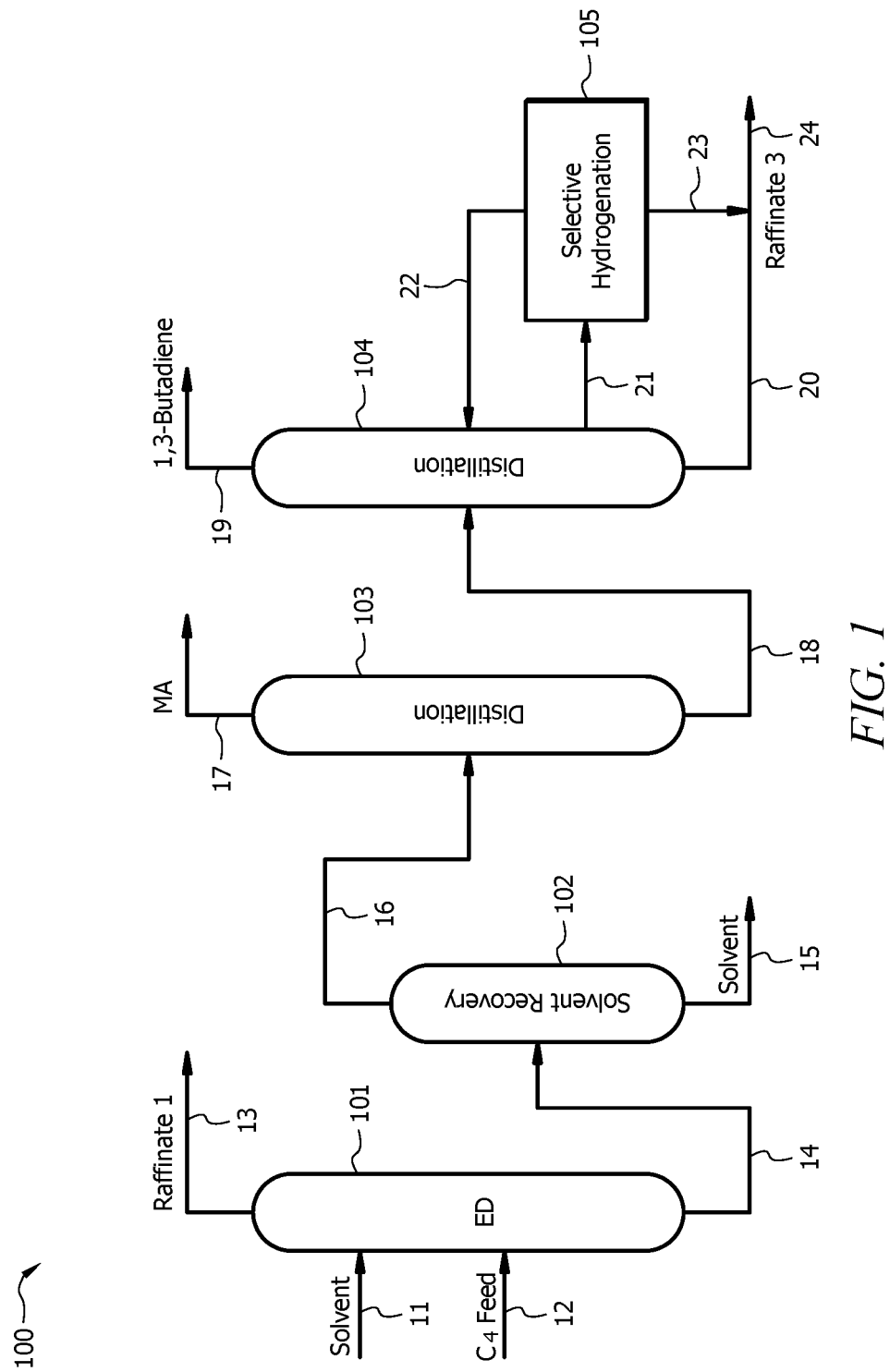
FIG. 1 shows a schematic diagram for a system for producing 1,3-butadiene, according to embodiments of the invention.

In embodiments of the invention, the system for producing 1,3-butadiene includes an extractive distillation column, one or more distillation columns, and a selective hydrogenation unit. With reference to FIG. 1, a schematic diagram is shown of system 100 for producing 1,3-butadiene. According to embodiments of the invention, system 100 includes extractive distillation column 101.

In embodiments of the invention, extractive distillation column 101 is configured to receive solvent stream 11 and $C_4$ hydrocarbon feed stream 12 comprising $C_4$ hydrocarbons therein. Extractive distillation column 101 is further configured to separate $C_4$ hydrocarbon feed stream 12 to produce first effluent stream 14 and first raffinate stream 13. According to embodiments of the invention, solvent stream 11 comprises a solvent including dimethylformamide (DMF), N-methyl-2-pyrrolidone (NMP), acetonitrile (ACN), or combinations thereof. $C_4$ hydrocarbon feed stream 12 may comprise n-butane, isobutane, isobutylene, 1-butene, 2-butenes, 1,3-butadiene, 1,2-butadiene, $C_4$ acetylenes, or combinations thereof. $C_4$ hydrocarbon feed stream 12 may further comprise methyl acetylene, $C_5+$ hydrocarbons, or combinations thereof. The $C_4$ acetylenes may include vinyl acetylene and/or ethyl acetylene. In embodiments of the invention, first effluent stream 14 is a bottom stream from extractive distillation column 101. First effluent stream 14 may comprise primarily the solvent, 1,3-butadiene, 1,2-butadiene, and $C_4$ acetylenes, collectively. First raffinate stream 13 may comprise n-butane, isobutane, isobutylene, 1-butene, 2-butene, and combinations thereof. In embodiments of the invention, solvent stream 11 is flowed into extractive distillation column 101 through an inlet disposed on upper half of extractive distillation column 101. In embodiments of the invention, $C_4$ hydrocarbon feed stream 12 is flowed into extractive distillation column 101 through an inlet disposed on lower half of extractive distillation column 101.

In embodiments of the invention, a bottom outlet of extractive distillation column 101 is in fluid communication with an inlet of solvent recovery unit 102 such that first effluent stream 14 flows from extractive distillation column 101 to solvent recovery unit 102. According to embodiments of the invention, solvent recovery unit 102 is configured to separate first effluent stream 14 to produce recovered solvent stream 15 and crude butadiene stream 16. In embodiments of the invention, recovered solvent stream 15 is a bottom stream from solvent recovery unit 102. Recovered solvent stream 15 comprises primarily the solvent. In embodiments of the invention, crude butadiene stream 16 comprises primarily 1,3-butadiene, $C_4$ acetylenes (vinyl acetylene and ethyl acetylene), collectively. Crude butadiene stream 16 may further include 2-butenes, methyl acetylene, 1,2-butadiene, $C_5+$ hydrocarbons, or combinations thereof. According to embodiments of the invention, solvent recovery unit 102 includes one or more distillation columns, one or more heat exchangers, one or more boil-off vessels, or combinations thereof.

According to embodiments of the invention, a top outlet of solvent recovery unit 102 is in fluid communication with first distillation column 103 such that crude butadiene stream 16 flows from solvent recovery unit 102 to first distillation column 103. In embodiments of the invention, first distillation column 103 is configured to separate crude butadiene stream 16 to form first overhead stream 17 and first bottom stream 18. In embodiments of the invention, first overhead stream 17 comprises methyl acetylene. First bottom stream 18 may comprise 1,3-butadiene, the $C_4$ acetylenes (vinyl acetylene and ethyl acetylene), $C_5+$ hydrocarbons, or combinations thereof.

According to embodiments of the invention, a bottom outlet of first distillation column 103 is in fluid communication with an inlet of second distillation column 104 such that first bottom stream 18 flows from first distillation column 103 to second distillation column 104. In embodiments of the invention, second distillation column 104 is configured to separate first bottom stream 18 to form second overhead stream 19 and second bottom stream 20. In embodiments of the invention, second overhead stream 19 comprises primarily 1,3-butadiene. Second bottom stream 20 comprises primarily $C_5+$ hydrocarbons. In embodiments of the invention, second distillation column 104 is further configured to form side stream 21 comprising primarily the $C_4$ acetylenes, collectively, including vinyl acetylene and ethyl acetylene.

According to embodiments of the invention, a side outlet of second distillation column 104 is in fluid communication with selective hydrogenation unit 105 such that side stream 21 flows from second distillation column 104 to selective hydrogenation unit 105. In embodiments of the invention, the side outlet of second distillation column 104 is located at 0 to 50% of total theoretical plate number of second distillation column counting from the bottom.

In embodiments of the invention, selective hydrogenation unit 105 is configured to selectively hydrogenate the $C_4$ acetylenes of side stream 21 to produce additional 1,3-butadiene stream 22 (a product stream) comprising primarily 1,3-butadiene and second raffinate stream 23 comprising $C_5$ to $C_8$ hydrocarbons. According to embodiments of the invention, selective hydrogenation unit 105 comprises one or more selective hydrogenation reactors and one or more separators (e.g., distillation columns). The one or more selective hydrogenation reactors may be configured to selectively hydrogenate the $C_4$ acetylenes of side stream 21 and produce a reactor effluent stream comprising 1,3-butadiene. The one or more separators may be configured to separate the reactor effluent stream to form additional 1,3-butadiene stream 22 and second raffinate stream 23. In embodiments of the invention, selective hydrogenation unit 105 includes a catalyst comprising Pd, Pt, $Al_2O_3$, Mn, Ni, Ag, or combinations thereof. In embodiments of the invention, selective hydrogenation unit 105 includes one or more fixed bed reactors. In embodiments of the invention, a first outlet of selective hydrogenation unit 105 is in fluid communication with an inlet of second distillation column 104 such that 1,3-butadiene stream 22 flows from selective hydrogenation unit 105 to second distillation column 104. In embodiments of the invention, second raffinate stream 23 is combined with second bottom stream 20 to form third raffinate stream 24. In embodiments of the invention, third raffinate stream 24 comprises 2-butenes, 1,2-butadiene, $C_5$ to $C_8$ hydrocarbons, or combinations thereof.

B. Method of Producing 1,3-butadiene

Figure 2:
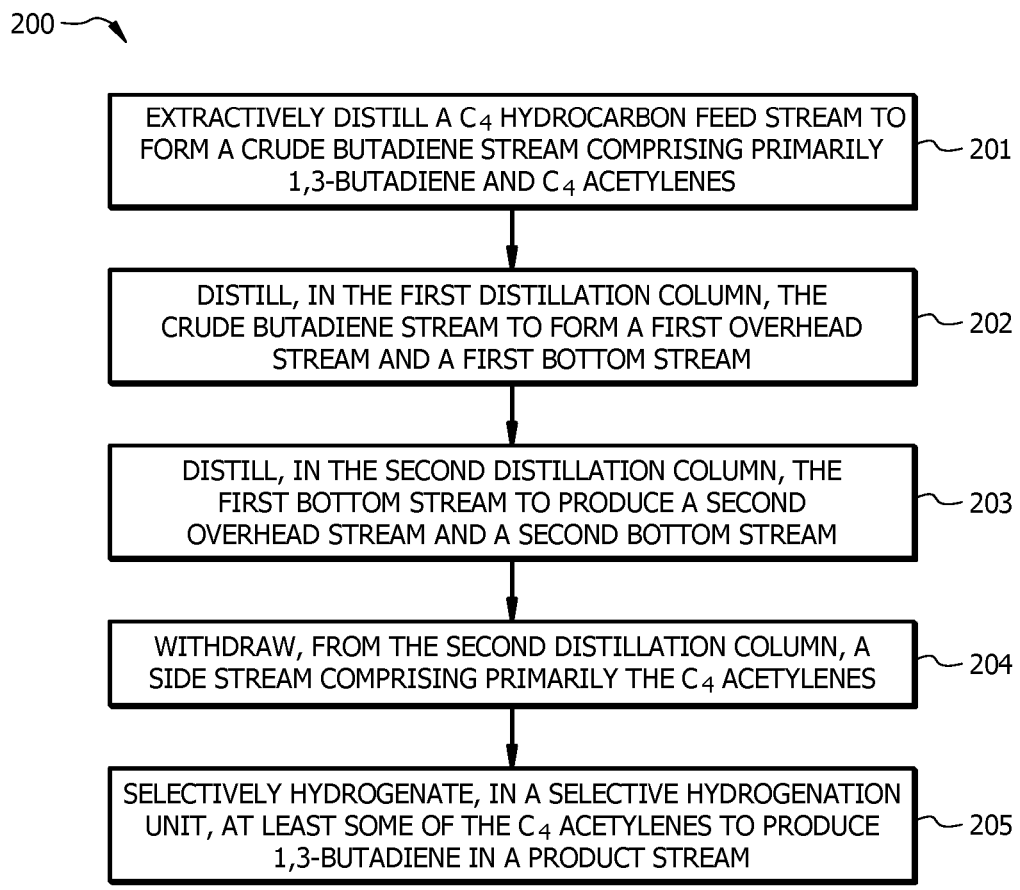
FIG. 2 shows a schematic flowchart for a method of producing 1,3-butadiene, according to embodiments of the invention.

Methods of producing 1,3-butadiene from a $C_4$ hydrocarbon feed stream have been discovered. Embodiments of the method are capable of reducing the production costs and capital expenditure for producing 1,3-butadiene compared to conventional methods. As shown in FIG. 2, embodiments of the invention include method 200 for producing 1,3-butadiene. Method 200 may be implemented by system 100, as shown in FIG. 1.

According to embodiments of the invention, as shown in block 201, method 200 includes extractive distilling of $C_4$ hydrocarbon feed stream 12 to form crude butadiene stream 16 comprising primarily 1,3-butadiene, and $C_4$ acetylenes, collectively, including vinyl acetylene and ethyl acetylene. In embodiments of the invention, $C_4$ hydrocarbon feed stream 12 comprises 0.1 to 10 wt. % butanes, 5 to 35 isobutene, 5 to 35 wt. % 1-butene, 1 to 15 wt. % 2-butenes, 0.01 to 5 wt. % methyl acetylene, 0.01 to 5 wt. % 1,2 butadiene, 25 to 60 wt. % 1,3 butadiene, 0.1 to 10 wt. % vinyl acetylene, and 0.1 to 10 wt. % ethyl acetylene. In embodiments of the invention, $C_4$ hydrocarbon feed stream 12 includes a $C_4$ hydrocarbon stream separated from an effluent of a steam cracking unit.

In embodiments of the invention, the extractive-distilling at block 201 includes flowing solvent stream 11 and $C_4$ hydrocarbon feed stream 12 to extractive distillation column 101 under operating conditions sufficient to produce first raffinate stream 13 and first effluent stream 14. The extractive-distilling at block 201 further includes separating first effluent stream 14 in solvent recovery unit 102 to produce recovered solvent stream 15 and crude butadiene stream 16. According to embodiments of the invention, solvent stream 11 and $C_4$ hydrocarbon feed stream 12 have a flowrate ratio in a range of 5 to 10 and all ranges and values there between including ranges of 5 to 6, 6 to 7, 7 to 8, 8 to 9, and 9 to 10. In embodiments of the invention, solvent stream 11 is flowed into an upper half portion of extractive distillation column 101. $C_4$ hydrocarbon feed stream 12 may be flowed into a lower half portion of extractive distillation column 101. In embodiments of the invention, extractive distillation column 101 is operated at an overhead boiling range of 25 to 45° C. and all ranges and values there between including ranges of 25 to 27° C., 27 to 29° C., 29 to 31° C., 31 to 33° C., 33 to 35° C., 35 to 37° C., 37 to 39° C., 39 to 41° C., 41 to 43° C., and 43 to 45° C. Extractive distillation column 101 may be operated at a reboiler range of 120 to 250° C. and all ranges and values there between including ranges of 120 to 130° C., 130 to 140° C., 140 to 150° C., 150 to 160° C., 160 to 170° C., 170 to 180° C., 180 to 190° C., 190 to 200° C., 200 to 210° C., 210 to 220° C., 220 to 230° C., 230 to 240° C., and 240 to 250° C. Extractive distillation column 101 may be operated at an operating pressure of 5 to 10 bara and all ranges and values there between including ranges of 5 to 5.5 bara, 5.5 to 6 bara, 6 to 6.5 bara, 6.5 to 7 bara, 7 to 7.5 bara, 7.5 to 8 bara, 8 to 8.5 bara, 8.5 to 9 bara, 9 to 9.5 bara, and 9.5 to 10 bara.

In embodiments of the invention, first effluent stream 14 comprises 10 to 35 wt. % 1,3-butadiene, 0.1 to 2 wt. % $C_4$ acetylenes, and 60 to 90 wt. % of the solvent. In embodiments of the invention, solvent recovery unit 102 is a distillation column. Solvent recovery unit 102 may be operated at an overhead boiling range of 40 to 100° C. and all ranges and values there between including ranges of 40 to 50° C., 50 to 60° C., 60 to 70° C., 70 to 80° C., 80 to 90° C., and 90 to 100° C. Solvent recovery unit 102 may be operated at a reboiler range of 120 to 300° C. and all ranges and values there between including ranges of 120 to 130° C., 130 to 140° C., 140 to 150° C., 150 to 160° C., 160 to 170° C., 170 to 180° C., 180 to 190° C., 190 to 200° C., 200 to 210° C., 210 to 220° C., 220 to 230° C., 230 to 240° C., 240 to 250° C., 250 to 260° C., 260 to 270° C., 270 to 280° C., 280 to 290° C., and 290 to 300° C. Solvent recovery unit 102 may be operated at an operating pressure of 1.2 to 8 bar and all ranges and values there between including ranges of 1.2 to 2.0 bar, 2.0 to 3.0 bar, 3.0 to 4.0 bar, 4.0 to 5.0 bar, 5.0 to 6.0 bar, 6.0 to 7.0 bar, and 7.0 to 8.0 bar. Crude butadiene stream 16 may comprise 85 to 95 wt. % 1,3-butadiene and 5 to 15 wt. % $C_4$ acetylenes. Crude butadiene stream 16 may further comprise 0.1 to 1 wt. % 2-butenes, 0.01 to 0.1 wt. % methyl acetylene, 0.01 to 0.05 wt. % 1,2-butadiene, and 0.1 to 1 wt. % $C_5$+ hydrocarbons According to embodiments of the invention, recovered solvent stream 15 can be recycled to extractive distillation column 101.

According to embodiments of the invention, as shown in block 202, method 200 comprises distilling, in first distillation column 103, crude butadiene stream 16 to form first overhead stream 17 and first bottom stream 18. First overhead stream 17 may comprise primarily methyl acetylene. First bottom stream 18 may comprise 85 to 95 wt. % 1,3-butadiene, 5 to 15 wt. % $C_4$ acetylenes including 3 to 12 wt. % vinyl acetylene and 2 to 3 wt. % ethyl acetylene. First bottom stream 18 may further include $C_5$+ hydrocarbons. In embodiments of the invention, first distillation column 103 is operated at an overhead boiling range of 25 to 45° C. and all ranges and values there between including ranges of 25 to 27° C., 27 to 29° C., 29 to 31° C., 31 to 33° C., 33 to 35° C., 35 to 37° C., 37 to 39° C., 39 to 41° C., 41 to 43° C., and 43 to 45° C. First distillation column 103 may be operated at a reboiler range of 40 to 70° C. and all ranges and values there between. First distillation column 103 may be operated at an operating pressure of 3 to 8 bara and all ranges and values there between including ranges of 3 to 3.5 bara, 3.5 to 4 bara, 4 to 4.5 bara, 4.5 to 5 bara, 5 to 5.5 bara, 5.5 to 6 bara, 6 to 6.5 bara, 6.5 to 7 bara, 7 to 7.5 bara, and 7.5 to 8 bara.

According to embodiments of the invention, as shown in block 203, method 200 comprises distilling, in second distillation column 104, first bottom stream 18 to produce second overhead stream 19 and second bottom stream 20. In embodiments of the invention, second overhead stream 19 includes 99.50 to 99.95 wt. % 1,3-butadiene and all ranges and values there between. Second bottom stream 20 may include primarily $C_5$+ hydrocarbons. In embodiments of the invention, second distillation column 104 is operated at an overhead boiling range of 25 to 45° C. and all ranges and values there between including ranges of 25 to 27° C., 27 to 29° C., 29 to 31° C., 31 to 33° C., 33 to 35° C., 35 to 37° C., 37 to 39° C., 39 to 41° C., 41 to 43° C., and 43 to 45° C. Second distillation column 104 may be operated at a reboiler range of 40 to 70° C. and all ranges and values there between including ranges of 40 to 42° C., 42 to 44° C., 44 to 46° C., 46 to 48° C., 48 to 50° C., 50 to 52° C., 52 to 54° C., 54 to 56° C., 56 to 58° C., 58 to 60° C., 60 to 62° C., 62 to 64° C., 64 to 66° C., 66 to 68° C., and 68 to 70° C. Second distillation column 104 may be operated at an operating pressure of 3 to 8 bara and all ranges and values there between including ranges of 3 to 3.5 bara, 3.5 to 4 bara, 4 to 4.5 bara, 4.5 to 5 bara, 5 to 5.5 bara, 5.5 to 6 bara, 6 to 6.5 bara, 6.5 to 7 bara, 7 to 7.5 bara, and 7.5 to 8 bara.

According to embodiments of the invention, as shown in block 204, method 200 comprises withdrawing, from second distillation column 104, side stream 21 comprising primarily $C_4$ acetylenes including vinyl acetylene, and/or ethyl acetylene. In embodiments of the invention, side stream 21 comprises 5 to 25 wt. % $C_4$ acetylenes. In embodiments of the invention, at block 204, side stream 21 is withdrawn at 0 to 50% of total theoretical plate number of second distillation column 104 counting from bottom thereof. In embodiments of the invention, withdrawing of side stream 21 at block 204 is configured to avoid vinyl acetylene self-decomposition and/or explosion in second distillation column 104. In embodiments of the invention, a flowrate ratio between first bottom stream 18 and side stream 21 is in a range of 0.01 to 0.2 and all ranges and values there between including ranges of 0.01 to 0.02, 0.02 to 0.03, 0.03 to 0.04, 0.04 to 0.05, 0.05 to 0.06, 0.06 to 0.07, 0.07 to 0.08, 0.08 to 0.09, 0.09 to 0.10, 0.10 to 0.11, 0.11 to 0.12, 0.12 to 0.13, 0.13 to 0.14, 0.14 to 0.15, 0.15 to 0.16, 0.16 to 0.17, 0.17 to 0.18, 0.18 to 0.19, and 0.19 to 0.20.

According to embodiments of the invention, as shown in block 205, method 200 comprises selectively hydrogenating, in selective hydrogenation unit 105, at least some of the $C_4$ acetylenes including the vinyl acetylene, and/or the ethyl acetylene of side stream 21 to produce additional 1,3-butadiene in a product stream (additional 1,3-butadiene stream 22). In embodiments of the invention, selectively hydrogenating at block 205 further produces second raffinate stream 23 comprising $C_5$ to $C_8$ hydrocarbons. In embodiments of the invention, additional 1,3-butadiene stream 22 comprises 85 to 99 wt. % 1,3-butadiene and all ranges and values there between including ranges of 85 to 87 wt. %, 87 to 89 wt. %, 89 to 91 wt. %, 91 to 93 wt. %, 93 to 95 wt. %, 95 to 97 wt. %, and 97 to 99 wt. %. In embodiments of the invention, at block 205, selective hydrogenation unit 105 is operated at a reaction temperature of 50 to 200° C. and all ranges and values there between including 50 to 60° C., 60 to 70° C., 70 to 80° C., 80 to 90° C., 90 to 100° C., 100 to 110° C., 110 to 120° C., 120 to 130° C., 130 to 140° C., 140 to 150° C., 150 to 160° C., 160 to 170° C., 170 to 180° C., 180 to 190° C., and 190 to 200° C. Selective hydrogenation unit 105 may be operated at a reaction pressure of 5 to 25 bara and all ranges and values there between including ranges of 5 to 6 bara, 6 to 7 bara, 7 to 8 bara, 8 to 9 bara, 9 to 10 bara, 10 to 11 bara, 11 to 12 bara, 12 to 13 bara, 13 to 14 bara, 14 to 15 bara, 15 to 16 bara, 16 to 17 bara, 17 to 18 bara, 18 to 19 bara, 19 to 20 bara, 20 to 21 bara, 21 to 22 bara, 22 to 23 bara, 23 to 24 bara, and 24 to 25 bara. In embodiments of the invention, additional 1,3-butadiene stream 22 (a product stream) is flowed back to second distillation column 104. Additional 1,3-butadiene stream 22 may be separated in second distillation column 104 to produce additional 1,3-butadiene stream 22 in second overhead stream 19. In embodiments of the invention, second raffinate stream 23 may be combined with second bottom stream 20 to form third raffinate stream 24 comprising primarily $C_5+$ hydrocarbons.

Although embodiments of the present invention have been described with reference to blocks of FIG. 2, it should be appreciated that operation of the present invention is not limited to the particular blocks and/or the particular order of the blocks illustrated in FIG. 2. Accordingly, embodiments of the invention may provide functionality as described herein using various blocks in a sequence different than that of FIG. 2.

In the context of the present invention, at least the following 19 embodiments are described. Embodiment 1 is a method of producing 1,3 butadiene. The method includes extractive distilling of a $C_4$ hydrocarbon feed to form a crude butadiene stream containing 1,3 butadiene and one or more $C_4$ acetylenes. The method further includes distilling, by one or more distillation columns, the crude butadiene stream. The method still further includes withdrawing, from the one or more distillation columns, a side stream containing primarily the one or more $C_4$ acetylenes. The method also includes hydrogenating at least some of the $C_4$ acetylene of the side stream to produce 1,3 butadiene in a product stream. Embodiment 2 is the method of embodiment 1, wherein the $C_4$ hydrocarbon feed contains one or more butanes, 1,2-butadiene, 1,3-butadiene, vinyl acetylene, and ethyl acetylene and $C_5+$ hydrocarbons. Embodiment 2 is the method of embodiment 2, wherein the $C_4$ hydrocarbon feed stream contains 0.1 to 10 wt. % butane, 5 to 35 wt. % isobutene, 5 to 35 wt. % 1-butene, 1 to 15 wt. % 2-butenes, 0.01 to 5 wt. % methyl acetylene, 0.01 to 5 wt. % 1,2 butadiene, 25 to 60 wt. % 1,3 butadiene, 0.1 to 10 wt. % vinyl acetylene, and 0.1 to 10 wt. % ethyl acetylene. Embodiment 4 is the method of any of embodiments 1 to 3, wherein the $C_4$ acetylene includes vinyl acetylene and/or ethyl acetylene and the crude butadiene stream further contains 2-butenes, methyl acetylene, 1,2-butadiene, $C_5+$ hydrocarbons, or combinations thereof. Embodiment 5 is the method of any of embodiments 1 to 4, wherein the hydrogenating step includes selective hydrogenation of the vinyl acetylene and/or ethyl acetylene. Embodiment 6 is the method of any of embodiments 1 to 5, wherein the distilling step includes distilling, in a first distillation column, the crude butadiene stream to form a first overhead stream containing primarily methyl acetylene and a first bottom stream containing 1,3-butadiene, vinyl acetylene, ethyl acetylene, $C_5$ hydrocarbons, $C_5+$ hydrocarbons, or combinations thereof. The method further includes distilling, in a second distillation column, the first bottom stream to produce a second overhead stream containing primarily 1,3 butadiene and second bottom stream containing primarily $C_5+$ hydrocarbons. Embodiment 7 is the method of embodiment 6, wherein the side stream is withdrawn from the second distillation column. Embodiment 8 is the method of either of embodiments 6 or 7, wherein the first distillation column is operated at an overhead boiling range of 25 to 45° C., and a reboiler range of 40 to 70° C. Embodiment 9 is the method of any of embodiments 6 to 8, wherein the first distillation column is operated at an operating pressure in a range of 3 to 8 bara. Embodiment 10 is the method of any of embodiments 6 to 9, wherein the second distillation column is operated at an overhead boiling range of 25 to 45° C., and a reboiler range of 40 to 70° C. Embodiment 11 is the method of any of embodiments 6 to 10, wherein the second distillation column is operated at an operating pressure in a range of 3 to 8 bar. Embodiment 12 is the method of any of embodiments 6 to 11, further including flowing the product stream produced in the hydrogenating step to the second distillation column. Embodiment 13 is the method of any of embodiments 1 to 12, wherein the extractive-distilling is carried out at an overhead boiling range of 25 to 45° C. and re-boiler range of 120 to 250° C. Embodiment 14 is the method of any of embodiments 1 to 13, wherein the extractive-distilling is carried out at an operating pressure of 5 to 10 bara. Embodiment 15 is the method of any of embodiments 1 to 14, wherein the extractive-distilling is carried out using a solvent selected from the group including DMF, NMP, CAN, and combinations thereof. Embodiment 16 is the method of any of embodiments 1 to 15, wherein the hydrogenating is conducted at a reaction temperature of 50 to 200° C. Embodiment 17 is the method of any of embodiments 1 to 16 wherein the hydrogenating is conducted at an operating pressure of 5 to 25 bar. Embodiment 18 is the method of any of embodiments 1 to 17, wherein the hydrogenating is conducted at a weight hourly space velocity in a range of 5 to 30 $hr^{-1}$. Embodiment 19 is the method of any of embodiments 1 to 18, wherein the hydrogenating is conducted in presence of a catalyst selected from the group consisting of Pd on alumina, Pt, Mn, Ni, Ag, and combinations thereof.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method of producing 1,3 butadiene, the method comprising:
   extractive distilling of a $C_4$ hydrocarbon feed to form a crude butadiene stream comprising 1,3 butadiene and one or more $C_4$ acetylenes;
   distilling, by one or more distillation columns, the crude butadiene stream to recover butadiene, acetylene and raffinate;
   withdrawing, from the one or more distillation columns, a side stream comprising primarily the one or more $C_4$ acetylenes; and
   hydrogenating at least some of the $C_4$ acetylene of the side stream to produce 1,3 butadiene in a product stream;
   wherein the $C_4$ hydrocarbon feed comprises $C_5+$ hydrocarbons and one or more butanes, 1,2-butadiene, 1,3-butadiene, vinyl acetylene and ethyl acetylene; and
   wherein the hydrogenating is conducted at a pressure of from 9 to 25 bar.

2. The method of claim 1, wherein the $C_4$ hydrocarbon feed comprises one or more butanes, 1,2-butadiene, 1,3-butadiene, vinyl acetylene and ethyl acetylene.

3. A method of producing 1,3 butadiene, the method comprising:
   extractive distilling of a $C_4$ hydrocarbon feed to form a crude butadiene stream comprising 1,3 butadiene and one or more $C_4$ acetylenes;
   distilling, by one or more distillation columns, the crude butadiene stream to recover butadiene, acetylene and raffinate;
   withdrawing, from the one or more distillation columns, a side stream comprising primarily the one or more $C_4$ acetylenes; and
   hydrogenating at least some of the $C_4$ acetylene of the side stream to produce 1,3 butadiene in a product stream,
   wherein the $C_4$ hydrocarbon feed comprises one or more butanes, 1,2-butadiene, 1,3-butadiene, vinyl acetylene, and ethyl acetylene and $C_5$+ hydrocarbons; and
   wherein the $C_4$ hydrocarbon feed stream comprises 0.1 to 10 wt. % butane, 5 to 35 wt. % isobutene, 5 to 35 wt. % 1-butene, 1 to 15 wt. % 2-butenes, 0.01 to 5 wt. % methyl acetylene, 0.01 to 5 wt. % 1,2 butadiene, 25 to 60 wt. % 1,3 butadiene, 0.1 to 10 wt. % vinyl acetylene, and 0.1 to 10 wt. % ethyl acetylene.

4. The method of claim 1, wherein the $C_4$ acetylene includes at least one acetylene selected from the group consisting of vinyl acetylene and ethyl acetylene; and wherein the crude butadiene stream further comprises 2-butenes, methyl acetylene, 1,2-butadiene, $C_5$+ hydrocarbons, or combinations thereof.

5. The method of claim 1, wherein the hydrogenating step includes selective hydrogenation of the vinyl acetylene and/or ethyl acetylene.

6. The method of claim 1, wherein the distilling step comprises:
   distilling, in a first distillation column, the crude butadiene stream to form a first overhead stream comprising primarily methyl acetylene and a first bottom stream comprising 1,3-butadiene, vinyl acetylene, ethyl acetylene, $C_5$ hydrocarbons, $C_5$+ hydrocarbons, or combinations thereof; and
      distilling, in a second distillation column, the first bottom stream to produce a second overhead stream comprising primarily 1,3 butadiene and second bottom stream comprising primarily $C_5$+ hydrocarbons.

7. The method of claim 6, wherein the side stream is withdrawn from the second distillation column.

8. The method of claim 6, wherein the first distillation column is operated at an overhead boiling range of 25 to 45° C., and a reboiler range of 40 to 70° C.

9. The method of claim 6, wherein the first distillation column is operated at an operating pressure in a range of 3 to 8 bara.

10. The method of claim 6, wherein the second distillation column is operated at an overhead boiling range of 25 to 45° C., and a reboiler range of 40 to 70° C.

11. The method of claim 6, wherein the second distillation column is operated at an operating pressure in a range of 3 to 8 bar.

12. The method of claim 6, further comprising flowing the product stream produced in the hydrogenating step to the second distillation column.

13. The method of claim 1, wherein the extractive-distilling is carried out at an overhead boiling range of 25 to 45° C. and re-boiler range of 120 to 250° C.

14. The method of claim 1, wherein the extractive-distilling is carried out at an operating pressure of 5 to 10 bara.

15. The method of claim 1, wherein the extractive-distilling is carried out using a solvent selected from the group comprising DMF, NMP and ACN, and combinations thereof.

16. The method of claim 1, wherein the hydrogenating is conducted at a reaction temperature of 50 to 200° C.

17. The method of claim 1, wherein the hydrogenating is conducted at an operating pressure of 25 bar.

18. The method of claim 1, wherein the hydrogenating is conducted at a weight hourly space velocity in a range of 5 to 30 $hr^{-1}$.

19. The method of claim 1, wherein the hydrogenating is conducted in presence of a catalyst selected from the group consisting of Pd on alumina, Pt, Mn, Ni, Ag, and combinations thereof.

20. The method of claim 4, wherein the hydrogenating is conducted in presence of a catalyst selected from the group consisting of Pd on alumina, Pt, Mn, Ni, Ag, and combinations thereof.

\* \* \* \* \*